United States Patent [19]
Ejima et al.

[11] Patent Number: 6,084,076
[45] Date of Patent: Jul. 4, 2000

[54] METHOD OF REFOLDING HUMAN ACTIVIN A

[75] Inventors: Daisuke Ejima; Kunio Ono; Michiro Sasaki; Yuzuru Eto; Shigekatsu Tsuchiya, all of Kawasaki, Japan

[73] Assignee: Ajinomoto Co., Inc., Tokyo, Japan

[21] Appl. No.: 09/091,265

[22] PCT Filed: Dec. 19, 1996

[86] PCT No.: PCT/JP96/03700

§ 371 Date: Feb. 8, 1999

§ 102(e) Date: Feb. 8, 1999

[87] PCT Pub. No.: WO97/23638

PCT Pub. Date: Jul. 3, 1997

[30] Foreign Application Priority Data

Dec. 21, 1995 [JP] Japan ..................................... 7-333070

[51] Int. Cl.[7] .......................... C07K 14/475; C07K 1/06; A61K 38/18; C12N 15/09; C12P 21/04
[52] U.S. Cl. ......................... 530/399; 530/427; 435/69.4; 435/71.2
[58] Field of Search ..................... 530/350, 399, 530/427, 351; 435/694, 71.1, 71.2, 69.1

[56] References Cited

U.S. PATENT DOCUMENTS

| | | | |
|---|---|---|---|
| 4,798,885 | 1/1989 | Mason et al. ............................ | 530/350 |
| 5,144,006 | 9/1992 | Tam ........................................ | 530/345 |
| 5,650,494 | 7/1997 | Cerletti et al. .......................... | 530/399 |
| 5,658,876 | 8/1997 | Crowley et al. ............................ | 514/2 |

FOREIGN PATENT DOCUMENTS

| | | |
|---|---|---|
| 433225 | 6/1991 | European Pat. Off. . |
| 96/03432 | 2/1996 | WIPO . |
| 96/03433 | 2/1996 | WIPO . |

OTHER PUBLICATIONS

Calbiochem (Ed. Neugebauer, J.), "A Guide to the Properties and Uses of Detergents in Biology and Biochemistry", pp. 1–22, 1987.

Schlunegger et al., FEBS Lett., 303(1), "Crystallization and Preliminary X–Ray Analysis of Recombinant Human Transforming Growth Factor–β–2.", pp. 91–93, May 1992.

Schmelzer et al., J.Cell.Biochem., Suppl. 14D, "Purification and Partial Characterization of Different Forms of Recombinant Human Activin–A by RP–HPLC (Conference Abstract)", p. 36, Mar. 1990.

Gray et al., Science, 247(4948), "Requirement for Activin–A and Transforming Growth Factor–β–1 Pro–Regions in Homodimer Assembly", pp. 1328–1330, Mar. 1990.

Mason, A. J., Mol. Endocrinol. 8(3), "Functional Analysis of the Cysteine Residues of Activin A", pp. 325–332, Mar. 1994.

*Primary Examiner*—Jon P. Weber
*Attorney, Agent, or Firm*—Oblon, Spivak, McClelland, Maier & Neustadt, P.C.

[57] ABSTRACT

A method for industrially producing human activin A which comprises refolding a modified human activin A produced by a microorganism into natural-form human activin A having a biological activity. This method comprises the steps of: (a) solubilizing the modified human activin A with a modifier and then protecting the thiol groups with glutathione and/or sodium sulfite; and (b) dialyzing the protected modified human activin A with a refolding buffer, containing taurodexoycholic acid or its salts and then adding a thiol compound thereto conduct a disulfide bond interchange reaction.

12 Claims, No Drawings

METHOD OF REFOLDING HUMAN ACTIVIN A

The present application is a National Stage Application of International Application PCT/JP96/03700, filed on Dec. 19, 1996.

The following is the English translation of the Annexes to the International Preliminary Examination Report, Amended Sheets 26 and 27.

FIELD OF THE INVENTION

The present invention relates to a method of refolding denatured human activin A into natural-type human activin A having a biological activity. Natural-type human activin is a useful protein expected to be applied to pharmaceutical preparations etc.

BACKGROUND OF THE INVENTION

Human activin A is a homodimer protein consisting of 2 polypeptide chains composed of 116 amino acids, isolated from a culture supernatant of human leukemic cell strain THP-1 (IFO 50147). Its molecular weight is about 25,000 dalton, each polypeptide contains 9 Cys residues (that is, 18 Cys residues in the dimer) and there are 9 intramolecular and intermolecular disulfide bonds (Biochemical and Biophysical Research Communications, 142, 1095–1103, 1987).

Human activin A is purified and produced by repeatedly subjecting, to multi-stage chromatography, precipitation and concentration operation, a culture supernatant obtained after stimulation of human myelocytic leukemic cell THP-1 (IFO 50147) with phorbol ester ("Saibo Kogaku" (Cell Engineering), Separate Volume 4, pp. 48–58, 1988) or a culture supernatant of recombinant CHO cells highly producing human activin A, obtained by introduction of an expression vector having human activin A cDNA (Biochemical and Biophysical Research Communications, 151, 230–235, 1988). However, there are many problems where the production process involving purification of culture supernatants as the starting material derived from animal cells is used as an industrial production process.

That is, (1) because impurities which were secreted by animal cells as the producing host or derived from fetal bovine serum etc. previously added as medium ingredients should be removed at high degrees, the yield of purified human activin A remains extremely low; (2) as compared with the case where recombinant microorganisms are used as the producing host, productivity is extremely low, and highly productive animal cells or culture apparatuses are necessary to sufficiently supply the starting material to be purified; and (3) to culture the producing host, a high concentration of fetal bovine serum should be added or a serum-free medium containing growth factors etc. should be used. However, these are extremely expensive, and there is a problem with stable availability of constant quality essential for production. As described above, there are problems with low productivity etc. in the case where human activin A is produced using animal cells, and it is necessary to solve these problems in order to establish an industrial production process.

Conventionally, various attempts have been made to solve these problems. If a microorganism such as recombinant *E. coli* etc. is used as the producing host, its protein productivity is generally improved 100-fold or more as compared with that of animal cells, so it can be said that replacement of animal cells by microorganisms as the producing host is an effective means of improving productivity. However, the production of human activin A by *E. coli* results often in denatured human activin A having different intramolecular and/or intermolecular disulfide bonds to those of the natural-type (European Patent Application Publication (EP0222491), Japanese Patent Appln. Laid-Open Publication No. 119679/88).

As used herein, denatured human activin A refers to molecules with the polypeptide chain of human activin A but having lost both its tertiary structure and biological activity, such as those with intramolecular and/or intermolecular disulfide bonds cleaved to loose the tertiary structure thus forming a monomer structure, those with the disulfide bonds transferred to form a structure different from the natural type, or those polymerized via additional intermolecular disulfide bonds.

Because such denatured human activin A has no biological activity, the molecule should be reconstituted (refolded) so as to have the same tertiary structure as that of the natural-type protein. However, it is not easy or even not possible to refold some proteins, so it is very difficult to determine their refolding conditions. Even after examination, it is not always possible to determine suitable refolding conditions particularly for certain polymeric proteins or proteins containing a large number of disulfide bonds, thus making it difficult to determine the refolding conditions.

Natural-type human activin A possesses 9 intramolecular and intermolecular disulfide bonds, so it is extremely difficult to determine the conditions for refolding of denatured human activin A and there is no prior art on the method of refolding human activin A. Meanwhile, A. J. Mason et al. examined the relationship between the efficiency of secretory expression of activin A by use of animal cells and the structure of an expression vector therefor, they reported that besides a region for the amino acid sequence of activin A, a pro-sequence region is essential for refolding and secretion of activin A, and only the region for the amino acid sequence of activin A does not cause refolding or secretion (Science, 247, 1328–1330, 1990). This report suggests that the refolding of denatured human activin A expressed by microorganisms as the producing host is very difficult.

The object of the present invention is to provide a method of refolding denatured human activin A produced by microorganisms into natural-type human activin A having a biological activity in order to constitute industrial production of human activin A.

DISCLOSURE OF THE INVENTION

As a result of their study to solve these problems, the present inventors developed a method of refolding denatured human activin A into biologically active natural-type human activin A, which comprises the following steps (a) and (b):

(a) the step of protecting thiol groups in solubilized denatured human activin A with all thiol groups free, with glutathione and/or sodium sulfite; and (b) the step of conducting the exchange reaction of disulfide bonds by dialyzing the protected denatured human activin A-containing solution against a refolding buffer and then adding a thiol compound thereto; or (a) the step of protecting thiol groups in solubilized denatured human activin A with all thiol groups free, with glutathione and/or sodium sulfite; and (b) the step of conducting the exchange reaction of disulfide bonds by replacing the buffer for the protected denatured human activin A-containing solution by a refolding buffer containing a thiol compound.

Specifically, the present invention relates to a method of refolding denatured human activin A, wherein natural-type human activin A is obtained by:

(1) protecting thiol groups in solubilized denatured human activin A with all thiol groups free, with glutathione and/or sodium sulfite;
(2) replacing the buffer by a refolding buffer; and
(3) forming intramolecular and/or intermolecular disulfide bonds by adding a thiol compound thereto; or
(1) protecting thiol groups in solubilized denatured human activin A with all thiol groups free, with glutathione and/or sodium sulfite; and
(2) replacing the buffer by a refolding buffer containing a thiol compound to form intramolecular and/or intermolecular disulfide bonds, wherein the refolding buffer permits the structure of natural-type human activin A dissolved at a concentration of 0.1 mg/ml in the refolding buffer, when denatured by reduction with 0.2 mM dithiothreitol (DTT), to be maintained stably by 20% or more than by a Tris buffer (1.5M urea, 20 mM Tris-HCl, pH 8.5). According to the present invention, the biological activity of denatured human activin A can be efficiently recovered.

BEST MODE FOR CARRYING OUT THE INVENTION

Hereinafter, the present invention is described in detail.

The starting material used in the present invention is a culture containing denatured human activin A obtained by culturing a microorganism having a human activin A gene integrated therein, for example, recombinant *E. coli*. If *E. coli* is used as a producing host, almost all human activin A is accumulated as insoluble granules in the microorganism, and thus the granules may be used as the starting material.

The insoluble granules of human activin A recovered in a usual manner is suspended in an aqueous solution of EDTA (ethylenediaminetetraacetic acid) at a low concentration (1 to 10 mM) and then solubilized with the protein denaturant guanidine hydrochloride and/or urea. The concentrations of guanidine hydrochloride and urea are respectively 4 to 7M and 6 to 10M required generally to denature protein. The concentration of human activin A is not particularly limited, but a concentration as high as possible is preferred for the subsequent operation. In addition, the pH value is kept preferably at 6 or less to prevent formation of unnecessary bonds. The solubilization operation is completed by stirring at room temperature for 2 to 4 hours.

Then, a reducing agent is added at a concentration of 1 to 100 mM, preferably 5 to 40 mM, to the solution of solubilized human activin A, and the mixture is adjusted to pH 8 to 9 with 20 mM Tris-HCl and subjected to reduction reaction at 20 to 50° C. for 15 to 360 minutes to free its thiol groups that are Cys residues. As the reducing agent, it is possible to use compounds such as reduced glutathione, DTT (dithiothreitol), 2-mercaptoethanol etc. among which DTT is particularly preferable. The amount of DTT added is preferably 5 to 40 mM. If all thiol groups in denatured human activin A produced by microorganisms are free, this reduction reaction is not required.

Oxidized glutathione is added in an amount of 0.05 to 0.3M, preferably 0.08 to 0.16M to the solution of solubilized human activin A with all thiol groups free, and the mixture is left at 0 to 50° C. for 2 to 24 hours or more whereby the thiol groups are protected. Alternatively, sodium sulfite may be used in place of oxidized glutathione in sulfonation for protection of the thiol groups. In this case, to human activin A with all thiol groups free are added sodium sulfite at a final concentration of 0.05 to 0.5M, preferably 0.08 to 0.16M, and simultaneously sodium tetrathionate at a final concentration of 5 to 20 mM, preferably 8 to 16 mM, and the mixture is left at 0 to 50° C. for 2 to 24 hours. Alternatively, a mixture of oxidized glutathione and sodium sulfite may also be used.

The state of protection of thiol groups can be confirmed by reverse phase HPLC on a silica gel column with chemically bound butyl groups, such as Vydac214TP54 (4.6φ×250 mm, Separations group) (Biochemical and Biophysical Research Communications, 142, 1095–1103, 1987). It is preferable that the reagents used in the foregoing operation are dissolved in a solvent previously degassed completely, and an inert gas such as nitrogen, helium etc. is preferably charged as a gas phase over the reaction solution to inhibit oxidation by oxygen in air. To conduct the subsequent steps, the unreacted protective agent for thiol groups is preferably removed by dialysis etc. from the resulting solution of human activin A with protected thiol groups.

The buffer solution for human activin A with protected thiol groups, obtained by the above-described method, is then replaced by a refolding buffer, pH 7.5 to 10.5. The refolding buffer which can be used in the present invention is a buffer permitting the structure of natural-type human activin A dissolved at 0.1 mg/ml in the refolding buffer, when denatured by reduction with 0.2 mM dithiothreitol (DTT), to be maintained stably by 20% or more than by a Tris buffer (1.5M urea, 20 mM Tris-HCl, pH 8.5). The operation will be described below in detail. For replacing the buffer solution for protected human activin A by the refolding buffer, there is a method in which human activin A with protected thiol groups is applied to a gel filtration column, e.g. Sephadex G-25 (Pharmacia Biotech), previously equilibrated with the refolding buffer degassed sufficiently, and the protein fraction is recovered. Alternatively, it is also possible to use a method in which human activin A with protected thiol groups is introduced into a dialysis membrane, e.g. Spectra/Por membrane, No. 1 (Spectrum Medical Industries, Inc.) and then dialyzed against a 500-fold excess volume of sufficiently degassed refolding buffer at 0 to 20° C. for 3 to 24 hours or more.

Subsequently, formation of disulfide bonds in human activin A with protected thiol groups is achieved by adding a thiol compound. The thiol compound is added at a concentration of 1 to 10 mM, preferably 2 to 5 mM, to the human activin A-containing solution in the buffer replaced by the refolding buffer as described above, and the mixture is left at 0 to 50° C. for 0.5 to 14 days. Completion of its refolding and the recovery of its biological activity can be confirmed by the above-described reverse phase HPLC and biological activity measurement (for example, measurement of the differentiation inducing activity for Friend leukemia cells, Biochemical and Biophysical Research Communications, 142, 1095–1103, 1987). The thiol compound may be a thiol compound such as cysteine, reduced glutathione, DTT, 2-mercaptoethanol etc. among which cysteine or reduced glutathione is particularly preferable. Cysteine or reduced glutathione is added preferably at a concentration of 2 to 5 mM.

Formation of disulfide bonds can also be initiated simultaneously with replacement by the refolding buffer. Hydrochloric acid is added to human activin A with protected thiol groups until the pH value is decreased 2–4, thus terminating the exchange reaction of disulfide bonds. It is dialyzed at 0 to 20° C. for 3 to 24 hours against a 500-fold excess volume of 1 to 100 mM hydrochloric acid containing a denaturant such as urea or guanidine hydrochloride, whereby the unreacted protective agent for thiol groups is removed. It is diluted with the refolding buffer for satisfying the conditions described below and then left at 0 to 50° C. for 0.5 to 14 days. The above thiol compound shall previously be added at the same concentration as above to the refolding buffer so as to promote the formation of disulfide bonds.

The conditions for the refolding buffer are determined in the following manner. It is considered that the refolding of human activin A is achieved by securing the environment of the solvent for stabilizing the tertiary structure of human activin A, rather than creation of a mutant suitable for refolding. The stability of the high-order structure can be estimated by measuring chemical stability assumed to be correlated therewith. As used herein, the chemical stability means that there does not occur any typical change such as molecular association, aggregation and precipitation caused by transfer of originally formed disulfide bonds in the molecule.

First, natural-type human activin A dissolved in 1 mM HCl is dissolved in a buffer, pH 7.5 to 10.5, consisting of a combination of a denaturant, surface active agent, salt, organic acid, amino acid, sugar, organic solvent etc. The concentration of natural-type human activin A is adjusted to about 0.1 mg/mg. A reducing agent (e.g. DTT, 2-mercaptoethanol or reduced glutathione) which is about 50 equivalents based on natural-type human activin A is added to it and the mixture is left at room temperature for about 12 hours, and the amount of the remaining natural-type human activin A is determined by reverse phase HPLC. As the control, Tris buffer (1.5M urea, 20 mM Tris-HCl, pH 8.5) was used and the same reaction as above was conducted and the amount of the remaining natural-type is compared. The increase (%) in the remaining amount by the refolding buffer, as compared with the remaining amount when the Tris-HCl buffer (1.5M urea, 20 mM Tris-HCl, pH 8.5) was used, is expressed as the improvement in the remaining amount. The buffer conditions bringing about higher improvement in the amount of remaining human activin A are preferable for high chemical stability, that is, for stabilization of the tertiary structure of human activin A as well as for promotion of its refolding. Various compounds are combined to prepare buffers and experimentally screened, and as a result it was found that if a buffer permits the structure of natural-type human activin A, when denatured by reduction, to be maintained stably by 20% or more than by the Tris buffer (1.5M urea, 20 mM Tris-HCl, pH 8.5), then said buffer is suitable as the refolding buffer. That is, the buffer satisfying this condition (for permitting the structure to be maintained stably by 20% or more than by the Tris buffer (1.5M urea, 20 mM Tris-HCl, pH 8.5)) can be used as the refolding buffer in the present invention. Specifically, the refolding buffer satisfying this condition includes the following buffers:

(I) buffers adjusted to pH 7.5 to 10.5, preferably 8.5 to 9.5, having a buffering action at pH 7.5 to 10.5 and containing:
  (a) reagents in class A and/or class B shown in Table 1, 0.5- to 2-fold higher concentrations than in the table;
  (b) urea, 0.1 to 3M, preferably 0.5 to 1M;

(II) buffers adjusted to pH 7.5, preferably 8.5 to 9.5, having a buffering action at pH 7.5 to 10.5 and containing:
  (a) reagents in class A and/or class B shown in Table 1, 0.5- to 2-fold higher concentrations than in the table;
  (b) urea, 0.1 to 3M, preferably 0.5 to 1M;
  (c) reagents in class A, class B and/or class C shown in Table 3, 0.5 - to 2-fold higher concentrations than in the table. The buffer having a buffering action at pH 7.5 to 10.5 includes Tris buffer, trimethylenediamine buffer, ethanolamine buffer etc. Further, guanidine hydrochloride may be used at a concentration of 0.05 to 2M, preferably 0.1 to 1M in place of the above-mentioned urea.

EXAMPLES

Hereinafter, the present invention is described in more detail by reference to the Examples.

Example 1

Natural-type human activin A obtained by repeatedly subjecting a culture supernatant derived from recombinant CHO cells to chromatography (Biochemical and Biophysical Research Communications, 151, 230–235, 1988) was prepared at a concentration of 2 mg/ml in 1 mM HCl and then diluted at a final concentration of 0.1 mg/ml with 12 kinds of 20 mM Tris-HCl buffer (pH 8.5) containing a combination of urea (1.5M and 3.0M), NaCl (1.0M and 0M), and CHAPS (2%, 0.5%, and 0M). DTT was added thereto at a final concentration of 0.2 mM and each mixture was left at room temperature for 12 hours so that its reduction reaction proceeded, and the amount of remaining human actin A was determined by reverse phase HPLC (Vydac214TP54, 4.6φ×250 mm, produced by Separations group).

The buffer indicating the highest remaining amount was 20 mM Tris-HCl buffer, pH 8.5 containing 1.5M urea and 2% CHAPS.

Example 2

The refolding buffer screened in Example 1 was used for refolding of human activin A.

E. coli into which DNA coding for human activin A had been introduced was cultured in a synthetic medium (1 L), and the tryptophan promoter was induced with an acid whereby human activin A was accumulated as insoluble granules in the microorganism (European Patent Application Publication (EP0222491) and Japanese Patent Laid-Open Appln. Publication No. 119,679/88). A suspension of the granules (1 mM EDTA, pH 6 or less) was prepared in a usual manner, and urea was added at a final concentration of 8M and the mixture was stirred at room temperature for 3 hours whereby it was solubilized by denaturation (20 ml). It was prepared in 20 mM Tris-HCl, pH 8.5, and DTT was added at a final concentration of 20 mM and the mixture was heated at 37° C. for 30 minutes.

After it was confirmed by reverse phase HPLC that the intramolecular and intermolecular disulfide bonds in human activin A were completely reduced, and oxidized glutathione was added at a final concentration of 0.1M and the mixture was left at 5° C. for 15 hours. Formation of mixed bonds between human activin A and glutathione was confirmed by reverse phase HPLC, and the concentration of human activin A was adjusted to 0.1 mg/ml in a dilution buffer (8M urea, 20 mM Tris-HCl, pH 8.5). It was introduced into a dialysis membrane (Spectra/Por membrane, No. 1, produced by Spectrum Medical Industries, Inc.) and dialyzed at 5° C. for 15 hours against a 500-fold excess volume of the refolding buffer (1.5M urea; 20 mM Tris-HCl, pH 8.5; 2% CHAPS) selected in Example 1.

Cysteine was added at a final concentration of 3 mM to the dialysate which was then left at 5° C. for 3 days. Reconstitution of the tertiary structure of human activin A was confirmed by measurement of its biological activity (differentiation inducing activity for Friend leukemia cells). As a result, it could be confirmed that 24% of the introduced denatured human activin A mass had the biological activity (differentiation inducing activity for Friend leukemia cells).

It was adjusted to pH 3 with 10% TFA (trifluoroacetic acid) and purified to an electrophoretically single component by reverse phase HPLC (Vydac214TP54, 4.6φ×250 mm, produced by Separations group; elution with a gradient of acetonitrile).

Example 3

The reagents shown in Table 1 were added at the indicated concentrations to the Tris-HCl buffer (1.5M urea, 20 mM Tris-HCl, pH 8.5) and these were used in reduction reaction at room temperature for 12 hours in place of the Tris-HCl buffer in Example 1, and the amount of remaining natural-type human activin A was examined using reverse phase HPLC. The results are shown in Table 1. The increase (%) in the remaining amount by each refolding buffer, as compared with the remaining amount when the Tris-HCl buffer only (1.5M urea, 20 mM Tris-HCl, pH 8.5) was used in reduction reaction, is expressed as the improvement in the remaining amount. As a result, it was found that depending on the types of used reagents, there is a great difference in the improvement (%) in the remaining amount. That is, it was found that addition of the reagents in class A or B resulted in improvement of the amount of remaining natural-type human activin A, and particularly addition of 0.53% TDCA/Na salt resulted in significant improvement of its remaining amount.

TABLE 1

Improvement in the amount of remaining natural-type human activin A in reduction reaction

| Class | Reagents added to the refolding buffer | Improvement in amount of remaining natural-type human activan A |
|---|---|---|
| A | 0.53% TDCA/Na | +40% |
| B | 0.13% TDCA/Na<br>9.8%, 2%, 0.49% CHAPS<br>10%, 2.1% CHAPSO<br>2.5%, 0.6% CA/Na<br>4.2%, 0.9%, 0.2% DCA/Na<br>1.6%, 0.38% TCA/Na<br>0.12% digitonin<br>4.0% NG | +20 to 40% |
| C | 0.12% NG<br>0.66%, 2.8%, 13% OG<br>0.04%, 0.2%, Tween 80<br>0.04%, 0.2% Tween 20<br>0.12%, 0.03% sarcosyl<br>0.08%, 0.02% Triton X-100<br>0.05% Span 80<br>0.04%, 0.16% Brij 98<br>0.1%, 0.01% SB-12 | 0 to +20% |
| D | 0.4% SB-12<br>0.04%, 0.01% betaine<br>0.04%, 0.01% Amisoft LS-11<br>0.6% sarcosyl<br>0.004% CTAC<br>0.002% SDS | No change |

TABLE 1-continued

Improvement in the amount of remaining natural-type human activin A in reduction reaction

| Class | Reagents added to the refolding buffer | Improvement in amount of remaining natural-type human activan A |
|---|---|---|
| E | 0.02%, 1.0% SDS<br>0.04%, 1.8% CTAC | Reduction in the remaining amount |

Abbreviations
CA/Na: Cholic Acid Sodium Salt
CHAPS: 3-[(3-Cholamidopropyl)dimethylamino]-1-propanesulfonate
CHAPSO: 3-[(3-Cholamidopropyl)dimethylamino]-2-hydroxy-1-propanesulfonate
CTAC: Cethyltrimethylammonium chloride (Hexadecyltrimethylammonium chloride)
DCA/Na: Deoxycholic acid sodium salt
NG: n-Nonyl-β-D-glucopyranoside
OG: n-Octyl-β-D-glucopyranoside
SB-12: N-Dodecyl-N,N-dimethyl-3-ammonio-1-propanesulfonate
SDS: Sodium dodecyl sulfate (Sodium lauryl sulfate)
Span 80: Sorbitan monooleate
TCA/Na: Taurocholic acid sodium salt
TDCA/Na: Taurodeoxycholic acid sodium salt
Triton X-100: Polyethylene Glycol Mono-p-isooctylphenyl Ether
Tween 20: Polyoxyethylene sorbitan monolaurate
Tween 80: Polyoxyethylene sorbitan monooleate
Sarcosyl: N-Lauroylsarcosine sodium salt Then, the Tris-HCl buffer (1.5M urea, 20 mM Tris-HCl, pH 8.5) to which each reagent shown in Table 1 had been added was used as the refolding buffer and the refolding of denatured human activin A produced in $E.$ $coli$ was achieved according to Example 2. As a result, in the case where the reagents (D, E) which did not change or lowered the amount of remaining natural-type human activin A were used, the recovery of the biological activity (differentiation inducing activity for Friend leukemia cells) was not observed at all, while in the case where the reagents (A, B, C) which raised its remaining amount were used, the recovery of the biological activity correlated with the improvement in its remaining amount, i.e. the progress of refolding, was observed (Table 2). In particular, the buffer to which the reagents in class A and B were added was effective as the refolding buffer. That is, it is understood that when the natural-type human activin A was denatured by reduction, it can be effectively refolded with the buffer capable of stably maintaining 20% or more of its structure as the refolding buffer.

These results indicated that a buffer suitable for refolding can be screened by examining the remaining amount in the reaction of reduction and denaturation.

TABLE 2

| Biological Activity after Refolding | | | | | |
|---|---|---|---|---|---|
| Used Regents | A | B | C | D | E |
| Recovery of biological activity | +++ | ++ | + | − | − |

Example 4

The reagents shown in Table 3 were added to the Tris-HCl buffer (1.5M urea, 0.13% TDCA/Na, 20 mM Tris-HCl, pH 8.5) containing 0.13% TDCA/Na confirmed to be effective in Example 3 and the resulting buffers were used in reduction reaction at room temperature for 12 hours in place of the Tris buffer in Example 3, and the amount of the remaining natural-type human activin A was determined using reverse phase HPLC. The results are shown in Table 3. The increase (%) in the remaining amount by each refolding buffer, as compared with the remaining amount when the Tris-HCl buffer (1.5M urea, 0.13 % TDCA/Na, 20 mM Tris-HCl, pH 8.5) was used in reduction reaction, is expressed as the improvement in the remaining amount. As a result, it was found that depending on the types of used reagents, there is a great difference in the improvement (%) in the remaining amount. That is, it was found that addition of the reagents in class A, B or C resulted in improvement of the amount of remaining natural-type human activin A as compared with addition of sole TDCA/Na, and particularly addition of 1M arginine hydrochloride resulted in significant improvement of its remaining amount.

Accordingly, the buffer to which the reagents in class A or B in Table 1 were added and those in class A, B or C in Table 3 were further added are considered more effective as the refolding buffer.

TABLE 3

Improvement in the amount of remaining natural-type human activin A in reduction reaction

| Class | Reagents added to the refolding buffer | Improvement in amount of remaining natural-type human activan A |
|---|---|---|
| A | 1.0M arginine hydrochloride | +35% |
| B | 0.5M arginine hydrochloride<br>1.0M, 0.5M magnesium acetate<br>1.0M, 0.5M lithium chloride<br>1.0M sodium chloride<br>1.0M ammonium chloride<br>1.0M lithium bromide | +20% |
| C | 0.5M calcium acetate<br>0.5M calcium chloride<br>1.0M, 0.5M magnesium chloride<br>1.0M sodium chloride<br>1.0M sodium propionate | +10% |
| D | 0.1M arginine hydrochloride<br>0.5M strontium chloride<br>1.0M calcium acetate<br>1.0M potassium acetate<br>1.0M potassium chloride<br>1.0M sodium formate<br>5% hexylene glycol<br>5% glycerol<br>5% PEG300<br>5% PGE4000<br>5% mannitol<br>5% 2-propanol<br>5% acetonitrile<br>5% TFE<br>5% methanol | 0 to +10% |
| E | 1.0M ammonium acetate<br>0.5M sodium tartrate<br>0.5M sodium citrate | Reduction in the remaining amount |

Abbreviations
PEG: Polyethylene glycol
TFE: Trifluoroethanol

Example 5

Sodium sulfite was added at a final concentration of 0.1M to reduced human activin A prepared in the same manner as in Example 2, and sodium tetrathionate was added at a final concentration of 0.01M thereto, and the mixture was left at 5° C. for 15 hours. Formation of mixed disulfide bonds between human activin A and sulfite ions was confirmed by reverse phase HPLC, and the concentration of human activin A was adjusted to 0.1 mg/ml in a dilution buffer (8M urea, 20 mM Tris-HCl, pH 8.5). It was introduced into a dialysis membrane (Spectra/Por membrane, No. 1 (Spectrum Medical Industries, Inc.) and then dialyzed at 5° C. for 3 days against a 500-fold excess volume of the refolding buffer (1M urea; 0.53% TDCA/Na, 1M arginine hydrochloride, 20 mM Tris-HCl, pH 8.5). Cysteine was added at a final concentration of 3 mM to the dialysate which was then left at 5° C. for 3 days. The reconstitution of the tertiary structure of human activin A was confirmed by measurement of the biological activity (differentiation inducing activity for Friend leukemia cells). It was adjusted to pH 3 with 10% TFA and purified to an electrophoretically single component by reverse phase HPLC (Vydac214TP54, 22φ×250 mm, produced by Separations group; elution with a gradient of acetonitrile).

Example 6

Formation of mixed disulfide bonds between human activin A and glutathione was confirmed by reverse phase HPLC in the same manner as in Example 2, and hydrochloric acid was added it to decrease the pH to 3.0. It was introduced into a dialysis membrane (Spectra/Por membrane, No. 1 (Spectrum Medical Industries, Inc.) and then dialyzed against a 500-fold excess volume of 8M urea containing 40 mM hydrochloric acid at 5° C. for 15 hours. The dialysate was diluted with a buffer calculated such that the final concentration agreed with the composition of the refolding buffer (1.5M urea, 0.13% TDCA/Na, 0.1M arginine hydrochloride, 0.1M Tris-HCl, pH 8.5) and simultaneously the concentration of human activin A became 0.1 mg/ml, and then the mixture was left at 5° C. for 3 days. The reconstitution of the tertiary structure of human activin A was confirmed by measurement of the biological activity (differentiation inducing activity for Friend leukemia cells). It was adjusted to pH 3 with 10% TFA and purified to an electrophoretically single component by reverse phase HPLC (Vydac214TP54, 4.6φ×250 mm, produced by Separations group; elution with a gradient of acetonitrile).

Example 7

The following refolding buffers were used respectively in place of the refolding buffer used in Example 6 and the same procedure was carried out whereby the tertiary structure of human activin A was reconstituted and then it was purified to an electrophoretically single component.
Buffer 1: 1M urea; 0.53% TDCA/Na; 0.5M arginine hydrochloride; 20 mM Tris-HCl, pH 8.5
Buffer 2: 1M urea; 0.53% TDCA/Na; 1M sodium chloride; 20 mM Tris-HCl, pH 8.5
Buffer 3: 1M urea; 0.13% TDCA/Na; 1M arginine hydrochloride; 20 mM Tris-HCl, pH 8.5
Buffer 4: 1M urea; 0.13% TDCA/Na; 0.5M arginine hydrochloride; 20 mM Tris-HCl, pH 8.5
Buffer 5: 1M urea; 0.13% TDCA/Na; 0.5M calcium acetate; 20 mM Tris-HCl, pH 8.5

Example 8

The following refolding buffers were used respectively in place of the refolding buffer used in Example 6 and the same procedure was carried out whereby the tertiary structure of human activin A was reconstituted, and it was then purified to an electrophoretically single component.
Buffer 6: 0.5M guanidine hydrochloride; 0.53% TDCA/Na; 0.5M arginine hydrochloride; 20 mM Tris-HCl, pH 8.5
Buffer 7: 0.5M guanidine hydrochloride; 0.53% TDCA/Na; 1M sodium chloride; 20 mM Tris-HCl, pH 8.5
Buffer 8: 0.5M guanidine hydrochloride; 0.13% TDCA/Na; 1M arginine hydrochloride; 20 mM Tris-HCl, pH 8.5
Buffer 9: 0.5M guanidine hydrochloride; 0.13% TDCA/Na; 0.5M arginine hydrochloride; 20 mM Tris-HCl, pH 8.5

Buffer 10: 0.5M guanidine hydrochloride; 0.13% TDCA/Na; 0.5M calcium acetate; 20 mM Tris-HCl, pH 8.5

Industrial Applicability

As described above, denatured human activin A can be refolded into natural-type human activin A for the first time by the method of the present invention, and it became possible to recover the biological activity for denatured human activin A in the easy method. That is, natural-type human activin A which should be produced conventionally in eukaryotic cells as the producing host could be produced easily and inexpensively by recombinant microorganisms as the producing host

What is claimed is:

1. A method of refolding denatured human activin A into natural-type human activin A having a biological activity, comprising:
   (a) protecting thiol groups in solubilized denatured human activin A with all thiol groups free, with glutathione and/or sodium sulfite, and (b1) dialyzing the protected denatured human activin A against a refolding buffer and then adding a thiol compound thereto, to exchange disulfide bonds in the denatured activin A and produce the human activin A having a biological activity, wherein
   the refolding buffer contains containing taurodeoxycholic acid or a salt thereof, and
   the refolding buffer permits the structure of natural-type human activin A dissolved at a concentration of 0.1 mg/ml in the refolding buffer, when denatured by reduction with 0.2 mM dithiothreitol (DTT), to be maintained stably by 20% or more than by a Tris buffer containing 1.5M urea, 20 mM Tris-HCl, at pH 8.5.

2. The method of claim 1, wherein the refolding buffer has a pH of 7.5 to 10.5.

3. The method of claim 1, wherein the refolding buffer further comprises arginine or a salt thereof.

4. The method of claim 1, wherein the refolding buffer contains the sodium salt of taurodeoxycholic acid.

5. The method of claim 1, wherein the refolding buffer contains the sodium salt of taurodexoycholic acid.

6. The method of claim 1, wherein the refolding buffer contains 0.065 to 0.26% of the taurodeoxycholic acid or a salt thereof.

7. The method of claim 1, wherein the refolding buffer contains 0.265 to 1.06% of the taurodeoxycholic acid or a salt thereof.

8. A method of refolding denatured human activin A into natural-type human activin A having a biological activity, comprising:
   (a) protecting thiol groups in solubilized denatured human activin A with all thiol groups free, with glutathione and/or sodium sulfite, wherein the solubilized denatured human activin A is solublized in a first buffer, and
   (b) replacing the first buffer with a refolding buffer containing a thiol compound, to exchange disulfide bonds in the denatured activin A and produce the human activin A having a biological activity, wherein
   the refolding buffer contains containing taurodeoxycholic acid or a salt thereof, and
   the refolding buffer permits the structure of natural-type human activin A dissolved at a concentration of 0.1 mg/ml in the refolding buffer, when denatured by reduction with 0.2 mM dithiothreitol (DTT), to be maintained stably by 20% or more than by a Tris buffer containing 1.5M urea, 20 mM Tris-HCl, at pH 8.5.

9. The method of claim 8, wherein the refolding buffer has a pH of 7.5 to 10.5.

10. The method of claim 8, wherein the refolding buffer further comprises arginine or a salt thereof.

11. The method of claim 8, wherein the refolding buffer contains 0.065 to 0.26% of the taurodeoxycholic acid or a salt thereof.

12. The method of claim 8, wherein the refolding buffer contains 0.265 to 1.06% of the taurodeoxycholic acid or a salt thereof.

* * * * *